United States Patent [19]

Farren et al.

[11] Patent Number: 4,741,198
[45] Date of Patent: May 3, 1988

[54] THERMAL CONDUCTIVITY DETECTOR ASSEMBLY

[75] Inventors: Carl A. Farren, Placentia; James H. Crabtree, Long Beach, both of Calif.

[73] Assignee: Beckman Industrial Corporation, LaHabra, Calif.

[21] Appl. No.: 915,677

[22] Filed: Oct. 6, 1986

[51] Int. Cl.$^4$ ............................................. G01N 30/66
[52] U.S. Cl. .................................... 73/23.1; 73/27 R
[58] Field of Search ................. 73/23.1, 27 R; 55/386

[56] References Cited

U.S. PATENT DOCUMENTS

| | | |
|---|---|---|
| 3,480,397 | 11/1969 | Baumgartel . |
| 3,616,677 | 11/1971 | Oppegaard ......................... 73/27 R |
| 3,634,757 | 1/1972 | Monomakhoff ................ 73/27 R X |
| 4,088,458 | 5/1978 | Jourdan . |
| 4,164,862 | 8/1979 | Jackson .............................. 73/27 R |
| 4,594,879 | 6/1986 | Maeda et al. ........................ 73/27 R |

*Primary Examiner*—Stewart J. Levy
*Assistant Examiner*—Joseph W. Roskos
*Attorney, Agent, or Firm*—Plante Strauss Vanderburgh

[57] ABSTRACT

The present invention relates to a gas chromatography assembly comprising a high mass, thermally conductive body provided with at least one cell in which is disposed a resistance filament for the detection of a sample gas. Lines are provided for communication between the cell and sample gas and carrier gas from chromatographic separation columns. The conductive body is adapted to carry the separation columns in heat transfer relationship therewith. In accordance with the present invention, the assembly components, including the interior of the cell and the separation columns are heated with a single heating element, which is controlled by a single heating element control means. The temperature of the environment of the sensor, switching valves and the separation columns, are thus controlled through a single constant temperature control system. Each element of the assembly is provided with sufficient surface area at the point where it is joined with an adjacent element of the assembly to define a flame path of sufficient length to prevent the escape of a flame from between the contiguous elements.

16 Claims, 4 Drawing Sheets

THERMAL CONDUCTIVITY DETECTOR ASSEMBLY

FIELD OF THE INVENTION

This invention relates to constant resistance thermal conductivity detectors and more particularly to a thermal conductivity assembly particularly adapted for use in chromatography.

BACKGROUND OF THE INVENTION

In gas chromatography, components being analyzed are separated by injecting a precise amount of the gaseous or vaporized sample onto an analytical column. A carrier gas transports the sample through the column which is provided with a suitable packing material to provide selective separation of the sample components within the column. A suitable detector is provided to sense the tested for component or components as they elute from the column and to produce an appropriate output signal proportional to the component concentration in the sample. Various types of detectors are available for this purpose such as for example, flame ionization detectors, flame photometric detectors and thermal conductivity detectors. While each type of detector has certain advantages and disadvantages, thermal conductivity detectors have been found highly useful for industrial chromatography because they are easily maintained, safe to use and are highly sensitive to trace amounts of components.

Thermal conductivity detectors employ a heated metal filament or thermistor as a resistance element for sensing changes in the thermal conductivity of the test gas contacting the sensor. The sensor, which is heated to a predetermined temperature, is first contacted by the carrier gas which cools the resistance element at a given rate dependent upon the thermal conductivity of the carrier gas. Changes in temperature of the sensor are reflected both in its resistance and in the voltage and current required to maintain its temperature. As the test component elutes from the column and flows past the resistance element, the thermal conductivity of the test fluid which is different from the carrier fluid, will change the temperature of the resistance element which will again be reflected by changes in the voltage and current required to maintain its temperature. Such changes in current and/or voltage are recorded as a measure of the concentration of the test gas in the sample. It will be apparent, however, that thermal conductivity detectors are subject to several problems which can affect the results obtained using them. For example, thermal conductivity detectors are subject to a thermal lag as a result of heating and cooling the resistance element, and such thermal lag can result in loss of sensitivity and reduced response time for the detector element. Efforts to compensate for thermal lag have included reducing the dimensions of the resistance element and increasing the temperature at which the resistance element is operated. However, overheating of the resistance element can result in physical damage and ultimate destruction of the element. Replacement of the thermal conductivity element requires considerable maintenance and calibration of the equipment which may result in loss of production time if the apparatus is employed in monitoring an industrial process or the like. In addition to the foregoing, the design of the detector cell in which the resistance element is contained is also highly important since poor cell design can result in excessive heat loss from the resistance element and attendant erroneous results. Control of the temperature of the carrier and sample within the separation column is also highly important to prevent inadvertent condensation of the sample and a resulting change in its concentration as well as unwanted changes in the temperature of the atmosphere immediately adjacent the sensor due to the temperature of the carrier and sample. In this regard in certain prior art chromatographs, temperature control of the column and the cell has been accomplished by separately controlling the temperature of the detector block, the sensor and the separation column. With this approach, unless complicated circuitry and expensive control instrumentation are used, it is difficult to achieve close control of the respective temperatures of the detector block, the sensor and the separation columns. Fluctuation of these temperatures can result in instrument drift and loss of sensitivity. Efforts to control the column temperature and the temperature of the detector block using a single heater and controller have produced units of somewhat lower cost. However, such units generally fail to achieve the precise temperature control desired for best results and such units have been found unsafe to use with hydrogen carrier gas because of designed cost economics. This is highly undesirable as hydrogen gas is widely used as a carrier gas throughout the world because of its availability and desirable thermal conductivity characteristics.

SUMMARY OF THE INVENTION

The present invention relates to a gas chromatography assembly (G C assembly) comprising a high mass thermally conductive body provided with at least one cell in which is disposed a resistance filament for the detection of a sample gas. Means are provided for communication between the cell and sample gas and carrier gas from chromatographic separation columns. The conductive body is adapted to carry the separation columns in heat transfer relationship therewith.

In accordance with the present invention, the assembly components, including the interior of the cell and the separation columns are heated with a single heating element, which is controlled by a single heating element control means. The temperature of the environment of the sensor, switching valves and the separation columns, are thus controlled through a single constant temperature control system. The operating temperature of the resistance filament of the detector is controlled by a separate constant temperature power supply to provide a stable temperature differential between the detector filament and cell. The resistance thermal detector is located in close proximity to the detector body so that a high stability of temperature control can be achieved thus resulting in greatly improved signal to noise ratio. The greatly improved signal to noise ratio permits thermal conductivity measurements at very low concentrations of the test gas. All connections of the assembly are of flame proof design to permit the safe use of hydrogen carrier gas as well as for the testing of explosive or combustible gas mixtures.

In a preferred form of the invention the G C assembly comprises a heat transfer plate defining at least one heat transfer surface and a detector block, in which the cell is disposed, defining a corresponding heat transfer face mounted on the heat transfer plate with the corresponding heat transfer face contiguous with the heat transfer surface of the heat transfer plate for conduction of heat from the heat transfer plate to the detector block. Pressure resistant capillaries provide communication between the interior of the cell and a sample and carrier gas. The sensor is connected in a Wheatstone bridge circuit to a comparator for the detection of any bridge imbalance which is used as the output signal and to control power to the sensor to maintain constant sensor temperature and resistance. A resistance thermal detector is provided in the thermally conductive body adjacent to sensor housing for sensing changes in cell temperature. The resistance temperature detector is likewise in a Wheatstone bridge circuit and is connected through a comparator to a phase controller which controls the circuit phase going to a single heater unit carried by the conductive body. Responsive to changes in cell temperature the phase controller controls the output of the heater unit and the ambient temperature within the cell is controlled to less than 0.01° C. The same heater unit and circuitry controls the temperature of the separation columns and ancillary switching and flow control valves so that the sample and carrier gas temperatures are also maintained within closely controlled limits.

In a preferred form of the invention, at least a pair of sensors are disposed in separate cells within the detector block with one sensor operating at a lower temperature than the other sensor so that high concentration samples can be passed through the cell in which the sensor is at the lower temperature while samples with low concentrations of the test gas are passed through the sensor operating at the higher temperature. In this fashion overloading or desensitization of a sensor by exposing it to excessive concentrations of test gas is avoided and the sensor life is prolonged. As an alternative the separate sensors and cells can be operated for use with two different carrier gases which makes possible simultaneous detection of more than one species of test gas.

By close control of the ambient temperature of the cell itself in which the sensor is disposed as well as the temperature of the sensor element itself, the differential between the sensor temperature and ambient temperature of the cell is stabilized and maintained in a constant condition thus increasing sensor life and reducing thermal lag and resultant loss of sensitivity of the detector. In addition the detector response rate is improved, providing a sharper, cleaner curve and reducing tailing which is primarily due to thermal lag in the sensor.

BRIEF DESCRIPTION OF THE DRAWINGS

The invention will be more readily understood and the advantages thereof appreciated from the following detailed description of the invention and the accompanying drawings in which.

DETAILED DESCRIPTION OF THE INVENTION

Figure 1:
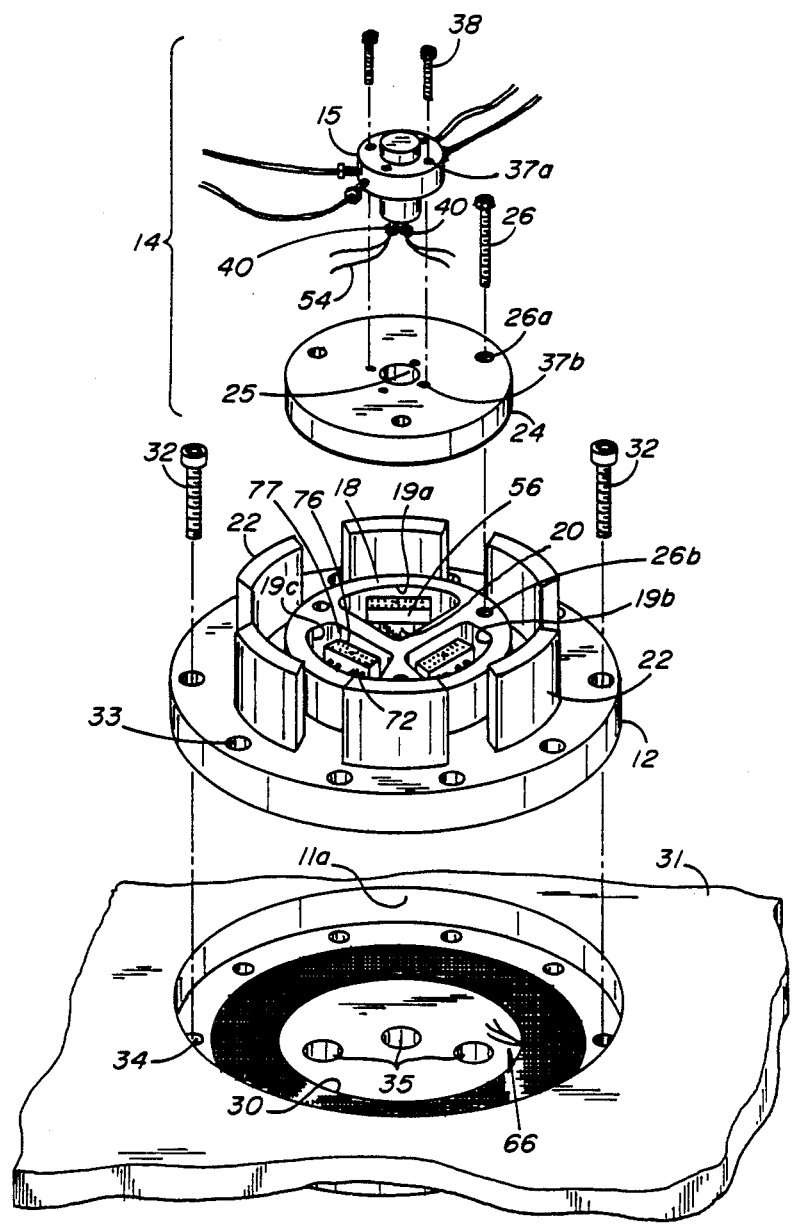
FIG. 1 is an exploded, perspective view of the gas chromatograph assembly of the present invention.
Figure 2:
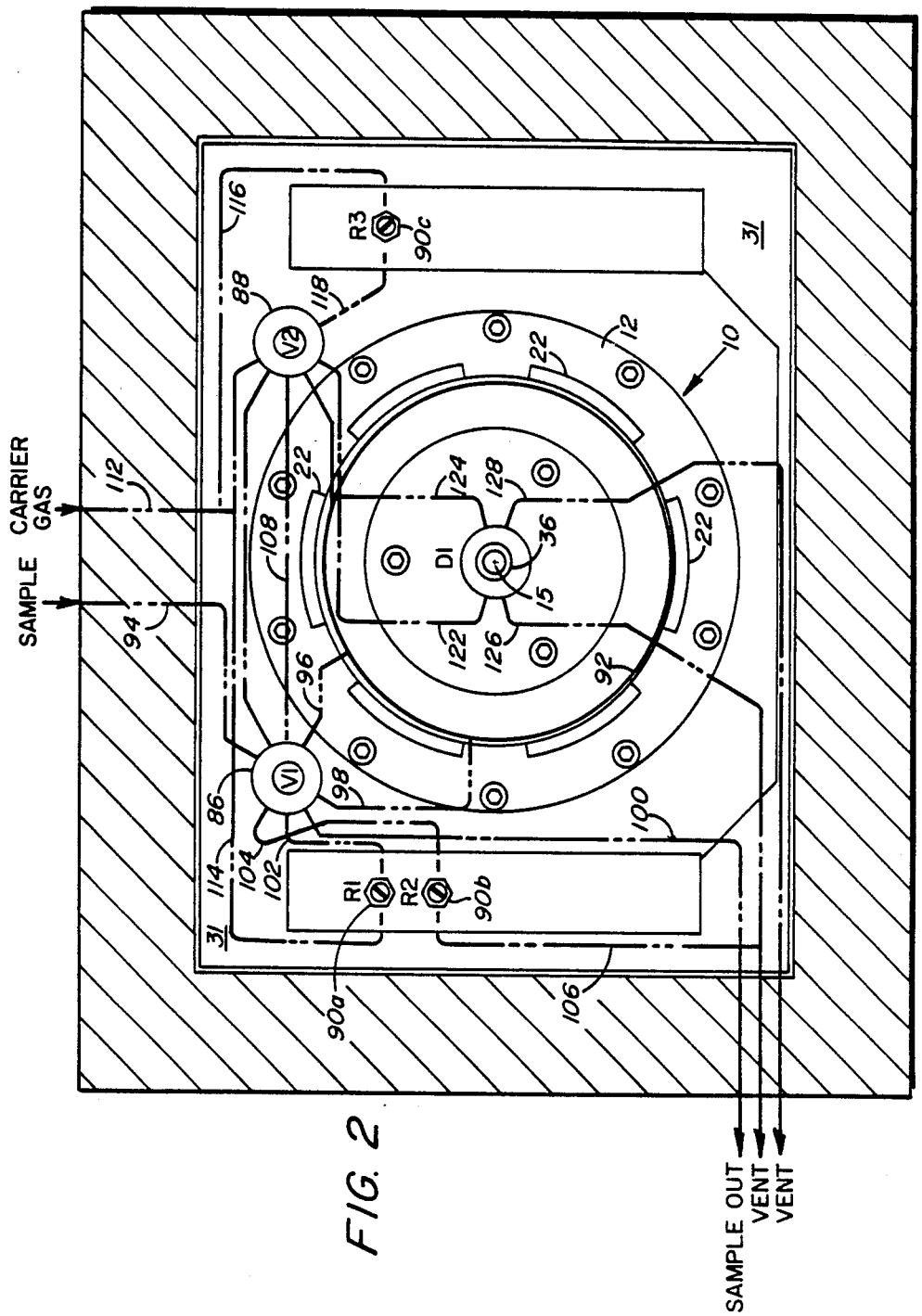
FIG. 2 is a top plan view of the assembly of FIG. 1 in enlarged scale schematically illustrating the flow of a test gas and carrier gas through the assembly.
Figure 3:
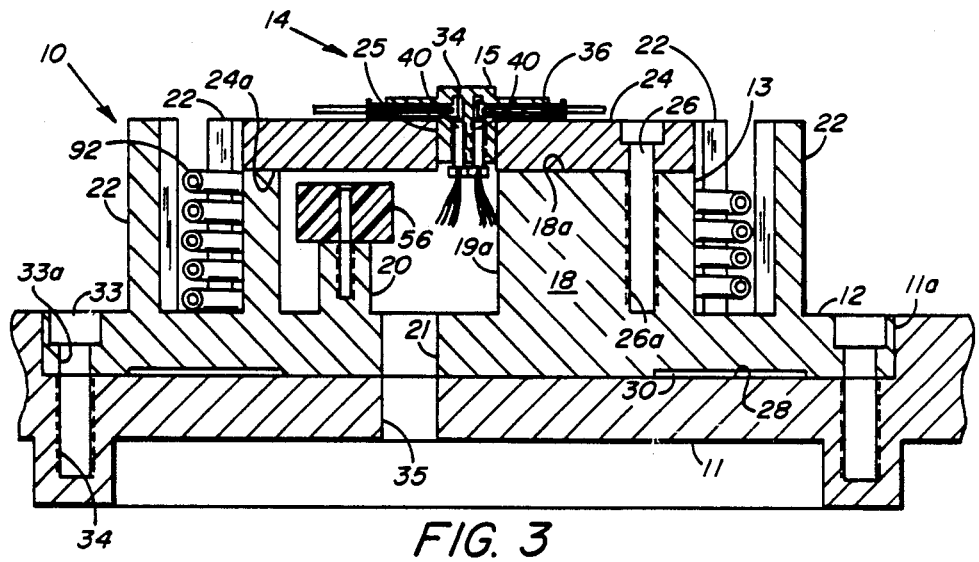
FIG. 3 is a sectional view through line 3—3 of FIG. 2.

Referring to FIGS. 1-3, the G C assembly, which is shown generally as 10, comprises a base plate 11 which is preferably provided with a bore 11a for receiving a heat transfer plate 12 which carries a detector block 14 as described more fully hereinafter. The base plate 11 is adapted for mounting on a suitable frame or the like to carry the G C assembly 10 and for mounting a case or cover for the G C assembly. The heat transfer plate 12 is provided with a raised center portion 18 the upper surface of which defines a heat transfer surface 18a. Disposed within the raised center portion 18 are cavities 19a, 19b, and 19c, the mouths of which open onto the surface 18a. The floor of each cavity 19a, 19b and 19c is provided with a boss 20 and a through running opening 21. The heat transfer plate 12 is also provided with projections or fins 22 which are spaced radially outwardly from the raised center portion 18 and as will be explained in more detail hereinafter, chromatographic columns 92 may be disposed therebetween. In an alternative embodiment the chromatographic columns 92 are wrapped around the external surfaces of the fins 22 for heat exchange between the columns and the fins. The detector block 14, comprises a cylindrically shaped cell body 15 received in a central bore 25 of a mounting plate 24. The lower surface of the mounting plate 24 defines a heat transfer face 24a which is contiguous with the surface 18a when the detector block 14 is mounted on the upper surface of the raised center portion 18 of the heat transfer plate 12. The area of contiguity of the surface 18a and the face 24a is sufficient to provide a flame path long enough to prevent a flame from escaping from between the heat transfer plate 12 and the detector block 14. Although any suitable means for retaining the detector block 14 on the heat transfer plate 12 may be utilized, it is highly preferred for safety and maintenance purposes to use shrouded bolts 26 which are received in threaded bores 26 in the heat transfer plate 12 so that the bolts cannot be accidentally broken off during use of the detector assembly, while at the same time the sensor housing can be readily removed for maintenance or other purposes by use of a special tool.

The opposite side of the heat transfer plate 12, which is received in the bore 11a of the base plate 11, is provided with an annular groove 28 for receiving and clamping an annular heating element 30. The heating element 30 may be of any material capable of uniformly heating the surface of the heat transfer plate 12. In the preferred embodiment, the heating element 30 comprises resistance heating elements laminated between compressible and flexible sheets of silicon rubber. In assembled condition the heating element 30 is slightly compressed between base plate 11 and heat transfer plate 12 providing uniform contact with the heat transfer plate thereby ensuring maximum heat transfer between the heating element and the heat transfer plate.

For the reasons set forth above, the detector assembly 10 is also mounted on the base plate 11 by shrouded bolts 32 which are disposed in through running, counterbored passages 33 disposed about the circumference of the heat transfer plate 12 and received in corresponding threaded bores 34 in the base plate. The floor of the bore 11a is provided with openings 35 which correspond with the openings 21 in the heat transfer plate to provide communication through the base plate 11 to each of the cavities 19a, 19b and 19c.

Figure 6:
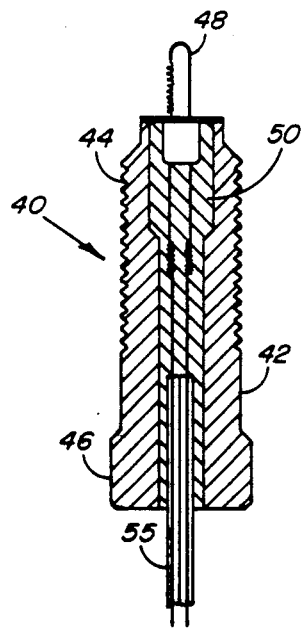
FIG. 6 is a sectional view in enlarged scale of a sensor assembly utilized in the invention.
Figure 7:
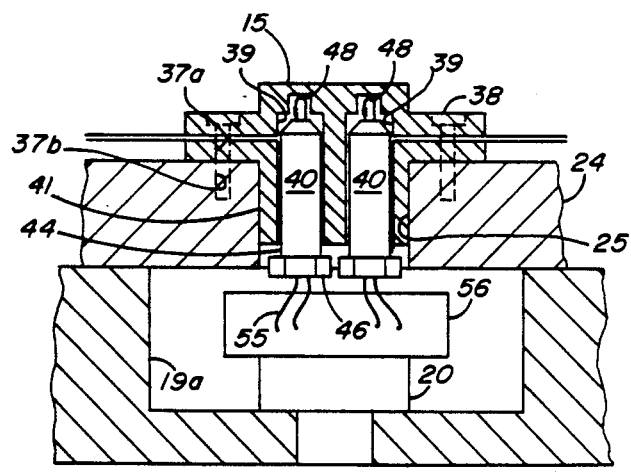
FIG. 7 is a sectional view in enlarged scale of a portion of the sensor housing assembly of FIG. 3.

As is more clearly illustrated in FIGS. 3, 6 and 7, the detector cell body 15 of the detector block 14 is provided with a pair of axially extending cells 39 in which are disposed sensor assemblies 40. The cell body 15 includes a collar 36 which is provided with threaded openings 37a which are aligned with corresponding threaded openings 37b in the mounting plate 24 and in which are disposed shrouded cap screws 38 for securing the cell body and the mounting plate. The under surface of the collar 36 and the surface 41 of the cell body 15 serve to increase the contact surface area between the cell body and the mounting plate 24 for maximum heat transfer and to create a flame path to prevent the escape of a flame. Each of the sensor assemblies 40 comprise an elongated bushing 42 which is provided with a threaded outer surface 44 for flame proof, threadable engagement with corresponding threads in the wall of the cell 39. The sensor bushing 42, which is open-ended and configured as a hexagonal bolthead 46 on one end, carries a sensor filament 48 which extends through and is retained in the sensor sleeve by a flame proof potting material 50, such as epoxy. When mounted in the cell body 15, the sensing filament 48 extends beyond the sensor sleeve 42 into the cell 39 and is exposed in the cell to sample gas and carrier gas. The end of the sensor bushing defining the hexagonal bolt head 46 extends into the cavity 19a of the raised portion 18 of the heat transfer plate and the wire leads 55 extending from the sensing filament 48 are connected to a terminal block 56 carried on the boss 20 in the cavity. A flame proof cable (not shown) from the sensor control circuitry extends through the aligned openings 35 and 21 in the base plate 11 and the heat transfer plate 12 respectively and is connected to the terminal block 56 to complete the electrical connection between the sensor assemblies 40 and the sensor control circuitry (FIG. 4) which will be described in more detail hereinafter.

Sample gas is lead into each of the cells 39 by means of capillary tubes 122 which extend through a passage 122a in the wall of the cell body 15 and open into the interior of the cell. As illustrated, the cell body 15 comprises a pair of cells 39, thus requiring two capillary tubes 122. A capillary tube 124 extends from the interior of each cell 39 to lead sample gas out of the cell. The capillary tubes 122 and 124 are preferably pressure tested and mounted in a flame proof manner in the wall of the cell body 15. The geometry of the cells 39 may be of several types which operate in accordance with commonly known principles. Thus, for example, it is well known that a high flow rate through the cell will decrease retention time. On the other hand, a high flow rate would not be desirable where a component of the sample gas is retained for a substantial period of time in the chromatographic column. Accordingly, the cells may be of the "through flow" type in which the gas flows at a fairly high rate through the cell or may be of the "diffusion" type in which the gas sample is retained in the cell. Alternatively, the cell geometries may be different for different cells in the sensor housing 14, thus adding to the flexibility and analytical possibilities of the detector housing of the present invention.

The heating element 30 is electrically connected to the heating element circuitry (FIG. 5) which will be described in more detail hereinafter, by leads 66 which extend from the heater element to a terminal block 72 which is disposed in the cavity 19c. A flame proof cable from the heater control circuitry extends through the aligned openings 21 and 35 to the terminal block 72 to complete the heater control circuit. A resistance thermal detector 76 is disposed in a chamber 77 which is defined in the wall of the cavity 19c immediately adjacent the sensor cells 39 in heat sensing relationship to the interior of the cavity 19a. Leads 78 from the thermal detector 76 are connected to the terminal block 72 to complete the connection between the thermal detector and the heater control circuitry.

Referring to FIG. 2, column switching valves 86 and 88 and flow restrictor valves 90a,b and c are mounted on the base plate 11 in heat radiating relationship to the heat transfer plate 12. The chromatographic column 92 is wound in helical fashion and disposed in the space defined between the fins 22 and the raised center portion 18 of the heat transfer plate 12. As previously mentioned, the chromatographic column may be wound about the outer surfaces of the fins 22 or chromatographic columns may be located in both positions. A sample inlet line 94 leads to the chromatographic column 92 from an injection port, not shown, through the column switching valve 86 and line 96. After passing through the chromatographic column 92 the sample is led back to the switching valve 86 by line 98. Depending upon the setting of the switching valve 86, the sample may also be sent directly out of the apparatus without analysis through line 100 or may be vented through line 104, restrictor valve 90a and line 106. Line 108 communicates with line 102 through valve 86 and leads sample to the switching valve 88. Carrier gas is lead into the system through line 112 from a source, not shown. Line 114 directly leads off from line 112 and communicates with line 108 through the restrictor valve 90a and the column switching valve 86. Line 116 which also leads directly off of line 112 conveys the carrier gas to the column switching valve 86 through flow restrictor valve 90c, and line 118, valve 88 and restrictor valve 90a. Test sample is directed to the detector cell body 15 from the valve 88 through lines 122 and 124 and vented through lines 126 and 128.

Although not shown, the entire G C assembly 10 and its ancillary coils, flow restrictor valves, switching valves and the like, are surrounded by a layer of thermal insulation and the entire assembly including insulation housed within a suitable casing.

Figure 4:
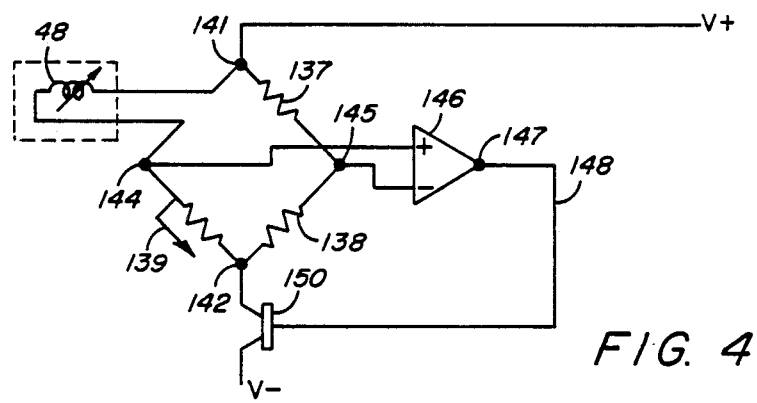
FIG. 4 is a schematic diagram of the electrical circuitry for heating and controlling the sensor filament.

Referring now to FIG. 4, the circuitry for detecting the signal output from the sensor assemblies 40 and for controlling the temperature of the respective resistor filaments 48 of the sensor assemblies is illustrated. The circuitry includes the sensor filament 48 and resistors 137, 138 and variable resistor 139 which are connected in respective legs of a Wheatstone bridge. The Wheatstone bridge is provided with input terminals 141 and 142 which are connected to a source of DC current, not shown. The Wheatstone bridge is also provided with output terminals 144 and 145 which connect the bridge to a differential amplifier 146 having a pair of differential terminals and an output terminal 147 which is connected to the input terminal 142 through line 148 and transistor 150.

Operationally the filament 48 is heated to a desired operational temperature and the bridge 134 is balanced with the carrier gas flowing past the resistance filament. As sample gas contacts the filament its different thermal conductivity results in an increase or decrease in filament temperature which in turn raises or lowers the resistance of the filament and unbalances the Wheatstone bridge. An increase in filament resistance increases the negative potential at input terminal 144 of the bridge 134 which causes the differential amplifier 146 to slew producing a reduction in current flow through the filament 48 and thus lowering its temperature to bring the bridge circuit back into balance. The change in polarity due to the increase in filament resistance is a measure of the amount of sample gas contacting the filament. A decrease in filament resistance has the opposite effect and calls for an increase in current to the filament.

The selection of circuitry for controlling sensor temperature and measuring output from the sensor is a matter of choice and numerous circuits, such as the one illustrated above, are known in the art for such purpose. In addition, the method used to power the detector may be a commonly used method including the application of a fixed voltage across the detector, the application of a constant current through the detector in which the detector output signal is a voltage imbalance at the bridge midpoint. Yet another method is the constant temperature method which maintains a balanced bridge by use of a feedback voltage control which is the output signal. This is the method described in connection with FIG. 4 above. Another method is the constant mean temperature technique which utilizes a bridge circuit within a second bridge circuit and feedback control. Its output signal is a voltage imbalance across the second bridge. The constant temperature method, illustrated in FIG. 4, is the preferred method for powering the detector.

Figure 5:
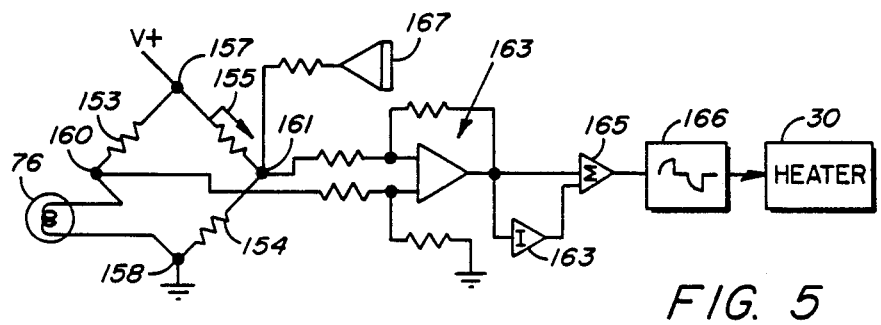
FIG. 5 is a schematic diagram of the electrical circuitry for controlling the heater element.

Referring to FIG. 5 there is schematically illustrated a circuit for controlling the heating element 30 in order to closely control the ambient temperature within the cells 39 in the sensor housing 14. This circuit also comprises a Wheatstone bridge comprising the temperature sensor 76 and, resistors 153 and 154 and variable resistor 155. The Wheatstone bridge circuit is connected to a source of current at supply terminal 157 and to ground at 158. Output from the Wheatstone bridge appears at output terminals 160 and 161 and the signal is conveyed to a differential amplifier shown generally as 163, and thence to integrator 164 and summation amplifier 165. The signal is then passed to an AC phase controller 166 where the current to the heating element 30 is controlled. Digital to analog connection 167, which may be computer operated, is used to control the set point of the AC phase controller 166.

In operation the Wheatstone bridge circuit is balanced by means of setting the variable resistor 155 to a sensor resistance to permit the heating element to reach the desired ambient temperature. The AC phase controller 166 permits the entire AC current to pass to the heating element which in turn heats the heat transfer plate 12. Heat from the heat transfer plate is conducted to the cells 39. When the desired temperature is reached, the bridge essentially is in balance and the summation amplifier 165 attains a stable output. As the ambient temperature rises above the desired temperature, the increase in temperature is sensed by the resistance temperature detector 76 and the signal therefrom unbalances the Wheatstone bridge circuit. A signal is sent to the differential amplifier 163 which through the integrator 164 and summation amplifier 165 signals the AC phase controller 166 to modify the current phase going to the heating element 30. The phase controller acts to cut back on the current phase which in turn causes the heating element 30 to reduce its heat output and results in reduction in the amount of heat conducted to the cells 39. The resultant cooling of the cells 39 also causes cooling in the temperature sensor 76 resulting in a reduction of its resistance bringing the bridge circuit back into balance.

Having described the operation of the filament sensor circuitry and the heater circuitry, the operation of the G C assembly 10 is now described. Both the sensor circuitry and the heater circuitry are set so as to be in balance with essentially static outputs when the sensor filaments 48 and the temperature sensor 76 are heated to the desired preselected temperature. It should be understood that the greater the difference in temperature between the filament sensor 48 and the ambient temperature of its respective cell, the greater the sensitivity of the sensor. By the same token a higher sensor temperature may result in shorter life for the filament requiring replacement of the filament and complete recalibration of the detector. Consequently, in the preferred embodiment of the invention, the sensor housing is provided with a pair of the cells 39. The sensor filament 48 in one of the sensor assemblies 40 is set to operate at a lower temperature than is the sensor filament of the other sensor assembly so that higher concentration samples are sent to the cell containing the sensor operating at a lower temperature while low concentration samples are directed to the cell containing the more sensitive sensor operating at the higher temperature. The ambient cell temperature is the same for both cells, so that only a single temperature sensor is required to maintain a substantially uniform temperature throughout the detector assembly 10. Likewise the fins 22 radiate heat to bring the chromatographic coils and the valves 86, 88 and 90$a,b$, and $c$, to essentially the same temperature as the cells. Bearing the foregoing in mind, when the sensor filament 48 in each of the sensor assemblies 40 has reached its preselected operating temperature, the carrier gas is permitted to flow through the chromatographic column 92 where it is heated by virtue of heat radiated from the fins 22. The cells 39 are brought to their temperature by virtue of the conductance of heat from the heating element 30 which is also conducted to the fins 22. In this manner a single heating element and control means is employed to effect the heating of both the cells 39 and the chromatographic columns 92. A sample is injected into line 96 and thence to column switching valve 86. Carrier gas which enters through line 112 flows through the restrictor valve 90a to the column switching valve 86 where it is mixed with the sample. The sample and carrier gas mixture then pass to the chromatographic column 92 in which there is disposed suitable packing material to effect the separation of components of the sample. The sample components exit the chromatographic column 92 and return to the column switching valve 86 and thence through line 108 to the column switching valve 88 where the components of the sample gas are directed through line 122 or line 124 to either of the cells 39 for detection by the respective sensor filament 48 disposed in the cell. The resulting signal is sent through the sensor circuitry as previously described.

Accordingly, in a preferred embodiment of the invention, the column switching valve 88 may be manually or automatically switched to alternate the flow through each of the cells 39 so that gross quantities of the test sample are detected in one cell with its sensor filament 48 operating at a relatively low temperature while trace quantities are detected in the other cell where the sensor filament 48 is operating at a relatively higher temperature. The choice of ambient cell temperature and filament temperature is dependent upon the nature of the samples being tested and the specific selection of temperatures is within the ordinary skill of the art. However, as previously mentioned, the greater the difference in temperature between the filament and its ambient temperature, the greater the sensitivity and response of the sensor. A second column, not shown, may be interposed between column switching valve 88 and line 124 to minimize the flow upset of valve switching and provide additional separation in another embodiment.

In an alternative mode of operation, the detector assembly 10 of the present invention can be used to detect more than one sample component. In this mode of operation the temperature of the sensor filaments 48 in the respective cells 39 are set dependent upon the thermal conductivity of the particular carrier gas and test specimen being sought. In this mode of operation the column switching valve 88 alternates to send flow of sample alternately through the cells. In this fashion each of the cells operate independently to detect a particular component. For example, cell 34 may be used to detect hydrogen in nitrogen, while cell 36 is utilized to detect nitrogen in a carrier gas of helium.

A detector assembly constructed in accordance with the invention has demonstrated the ability to provide one volt peaks for quantities of nitrogen in helium as low as 100 ppm. In the determination of nitrogen in helium carrier gas the filament temperature was maintained at 500° C. and the ambient cell temperature at 60° C. However the cell ambient temperature may be maintained between 50° C. to 180° C. while filament temperatures are normally maintained between 300° C. and 500° C.

While a preferred embodiment and modifications have been described in the foregoing description and illustrated in the drawings, it will be understood that minor changes may be made in the details of construction as well as in the combination and arrangement of the parts without departing from the spirit and scope of the invention as claimed.

What is claimed is:

1. A gas chromatography detector assembly comprising a thermally conductive body, sample separation means carried by said body in heat transfer relationship thereto, said body defining at least one cell having disposed therein a thermal conductivity sensor element, means for leading sample and carrier gas through said separation means into said cell for contact with said sensor and for leading fluids out of said cell after contact with said sensor, said sensor element being electrically connected to circuit means for controlling said sensor operating temperature and resistance and for controlling electrical power to said sensor responsive to the resistance of said sensor and to means for amplifying and displaying a signal received from said sensor, heater means in heat transfer relationship through said body with said cell and with said sample separation means and heater control circuitry including a temperature detector disposed in said body adjacent said cell for activating said heater means and for controlling the output thereof responsive to the temperature within said cell whereby the ambient temperature of said cell is maintained at a substantially constant preselected level resulting in a substantially improved signal to noise ratio.

2. The assembly of claim 1 wherein said heat conductive body defines a pair of cells, a thermal conductivity sensor being disposed in each of said cells, one of said sensors being maintained at a lower operating temperature than said other sensor.

3. The assembly of claim 1 wherein said thermally conductive body comprises a heat transfer plate defining at least one heat transfer surface and a detector block in which said cell is disposed and defining a corresponding heat transfer face mounted on said heat transfer surface with the corresponding heat transfer face contiguous thereto for conduction of heat from said heat transfer plate to said detector block.

4. The assembly of claim 3 wherein said heat transfer plate includes a central raised hub, the upper surface of which defines said heat transfer surface for mounting said detector block, at least one cavity disposed in said raised hub and having its mouth opening at said heat transfer surface, said cavity having disposed therein means for connecting said sensor element and said heater means to their respective electrical circuits and the mouth of said cavity being normally closed by the corresponding face of said detector block.

5. The assembly of claim 4 wherein said heat transfer plate further includes upstanding fin members spaced radially outwardly from said hub and a separation column is disposed between said hub and said fin members.

6. The assembly of claim 5 wherein a separation column is wound about the outer surface of said fin members.

7. The assembly of claim 3 wherein the area of contiguity between the heat transfer surface of said heat transfer plate and the corresponding face of said detector block defines a flame path sufficient to prevent the escape of a flame from between said detector block and said heat transfer plate.

8. The assembly of claim 3 wherein said detector block comprises a cylindrically shaped cell body and a mounting plate having a central bore for receiving said cell body, said cell body defining in the interior thereof at least one axially extending cell opening at one end of said cell body, the opposite end of said cell body being closed, a radially extending collar disposed on said cell body adjacent the closed end thereof, the surface of said mounting plate and said bore and the corresponding surfaces of said cell body in said bore and said collar being contiguous wherein the area of contiguity therebetween defines a flame path sufficient to prevent the escape of a flame from between said cell body and said mounting plate and means in said cell body defining ingress and egress of sample and carrier gas into and out of said cell.

9. The assembly of claim 8 wherein said thermally conductive body defines a pair of cells, each having a thermal conductivity sensor element disposed therein.

10. The assembly of claim 8 wherein said ingress and egress means for said cell comprise a pair of pressure resistant capillary tubes extending radially through said cell body to communicate with said cell, one of said tubes communicating with a source of sample and carrier gas and the other of said tubes communicating with a vent.

11. The assembly of claim 1 wherein said heater means comprises a single heater unit carried by said thermally conductive body in heat conductive relationship therewith.

12. The assembly of claim 11 wherein said heater unit is flexible and compressible.

13. The assembly of claim 11 wherein said heater unit is annularly shaped and is disposed in an annular groove provided on a surface of said thermally conductive body.

14. The assembly of claim 1 wherein said sensor element comprises a filament retained in one end of an open ended bushing and extending from one end thereof and leads connected to said filament extending through the opposite end of said bushing for electrical connection of said filament to said sensor circuitry, the outside diameter of said bushing being substantially the same as the internal diameter of said cell thereby to provide a substantially snug fit of said sensor element in said cell.

15. The sensor element of claim 14 wherein the inner wall of said cell and the outer surface of said bushing are provided with corresponding threaded elements for threadably retaining said sensor element in said cell.

16. The assembly of claim 1 wherein said separation means comprises at least one packed column in heat transfer relationship with said thermally conductive body for heating the contents thereof by said heating means.

* * * * *